(12) United States Patent
Gottlieb et al.

(10) Patent No.: US 10,585,068 B2
(45) Date of Patent: Mar. 10, 2020

(54) ULTRASONIC ELASTOMER CHARACTERIZATION

(71) Applicant: Cameron International Corporation, Houston, TX (US)

(72) Inventors: Emanuel Gottlieb, Upper St. Clair, PA (US); Hamid Salem, Katy, TX (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 90 days.

(21) Appl. No.: 15/649,737

(22) Filed: Jul. 14, 2017

(65) Prior Publication Data

US 2019/0017967 A1    Jan. 17, 2019

(51) Int. Cl.

| G01N 29/02 | (2006.01) |
|---|---|
| G01N 29/024 | (2006.01) |
| G01N 29/36 | (2006.01) |
| G01N 29/44 | (2006.01) |
| G01N 33/28 | (2006.01) |
| G01N 29/07 | (2006.01) |

(52) U.S. Cl.
CPC ........... *G01N 29/024* (2013.01); *G01N 29/07* (2013.01); *G01N 29/36* (2013.01); *G01N 29/44* (2013.01); *G01N 33/2835* (2013.01); *G01N 2291/011* (2013.01); *G01N 2291/0235* (2013.01); *G01N 2291/0258* (2013.01); *G01N 2291/02827* (2013.01); *G01N 2291/044* (2013.01)

(58) Field of Classification Search
CPC ...... G01N 29/024; G01N 29/36; G01N 29/44; G01N 33/2835; G01N 2291/011; G01N 2291/0235; G01N 2291/0258; G01N 2291/02827; G01N 2291/044; G01N 29/07

See application file for complete search history.

(56) References Cited

U.S. PATENT DOCUMENTS

| 5,164,548 A * | 11/1992 | Angehrn | E21B 47/0002 181/103 |
|---|---|---|---|
| 5,341,687 A * | 8/1994 | Stan | G01L 5/167 73/146 |
| RE37,065 E | 2/2001 | Grahn | |
| 6,446,494 B2 * | 9/2002 | Hastings | G01N 29/032 73/54.41 |
| 2009/0314088 A1 * | 12/2009 | Djordjevic | G01N 29/028 73/602 |
| 2010/0154560 A1 * | 6/2010 | Mueller | G01F 1/662 73/861.18 |

(Continued)

FOREIGN PATENT DOCUMENTS

RU    2196982 C2 *    1/2003

OTHER PUBLICATIONS

Report Information from ProQuest Dialog, Feb. 20, 2019 Machine Translation (Year: 2019).*

(Continued)

*Primary Examiner* — Francis C Gray
(74) *Attorney, Agent, or Firm* — Helene Raybaud

(57) ABSTRACT

A non-destructive method uses ultrasound measurements to determine some mechanical properties of an elastomeric material. The measurements can be made during manufacture of the elastomer for quality control purposes. The measurements can also be made on the elastomeric material in situ as part of a device to assess degradation of the elastomer over time.

20 Claims, 7 Drawing Sheets

(56) References Cited

U.S. PATENT DOCUMENTS

| | | | |
|---|---|---|---|
| 2015/0007651 A1* | 1/2015 | Reyes, III | E21B 34/16 |
| | | | 73/152.51 |
| 2015/0362305 A1* | 12/2015 | Ferrari | G01N 29/225 |
| | | | 33/503 |
| 2017/0276651 A1* | 9/2017 | Hall | G01B 17/02 |

OTHER PUBLICATIONS

Afifi et al., Ultrasonic properties of ENR-EPDM rubber blends. Polymer Bulletin, 50(1-2), pp. 115-122, 2003.

Biwa et al., Elastic properties of rubber particles in toughened PMMA: ultrasonic and micromechanical evaluation. Mechanics of Materials, 33(12), pp. 717-728, 2001.

Brown, Roger, Physical Testing of Rubber, Springer Science Business Media, 2006, p. 163.

Gabrielli et al., Measurements of ultrasonic absorption in rubber. II Nuovo Cimento (1955-1965), 1(3), pp. 103-413, 1955.

Jaunich et al., Monitoring the vulcanization of elastomers: Comparison of curemeter and ultrasonic online control. Polymer Testing, 28(1), pp. 84-88, 2009.

Jayaraman et al., Ultrasonic characterization of elastomers and elastometric composites. In NDE for Health Monitoring and Diagnostics, International Society for Optics and Photonics, pp. 397-403, Jun. 2002.

Kirchhoff et al., Measuring the state of cure of elastomers by using an ultrasonic technique. Kautschuk Gummi Kunststoffe, 55(7-8), 373-381, 2002.

Mott et al., The bulk modulus and Poissons ratio of "incompressible" materials. Journal of Sound and Vibration, 312 (4), pp. 572-575, 2008.

\* cited by examiner

ULTRASONIC ELASTOMER CHARACTERIZATION

TECHNICAL FIELD

The present disclosure relates to systems and methods for elastomer characterization. More specifically, the present disclosure relates to systems and methods that use ultrasound to characterize elastomeric material, such as rubber.

BACKGROUND

Elastomeric materials are used for a variety of applications in many different settings. In the oil and gas industry, elastomer material is used in many components including seals, donuts, and packers. During manufacture of such components it is important to maintain quality control of the material properties of the elastomer. For example, proper curing of the elastomer should be carried out in order meet mechanical specifications of the component. Furthermore, in many situations such as in the oil and gas industry, in situ monitoring the elastomer properties, such as for fatigue due to temperature and/or pressure cycling, is either impossible or impractical due to the inaccessibility of the component and/or a relatively high intervention cost.

SUMMARY

This summary is provided to introduce a selection of concepts that are further described below in the detailed description. This summary is not intended to identify key or essential features of the claimed subject matter, nor is it intended to be used as an aid in determining or limiting the scope of the claimed subject matter as set forth in the claims.

According to some embodiments, a system for characterizing elastomer material is described. The system includes: one or more ultrasonic transducers configured to transmit ultrasonic energy into an elastomer material and receive the ultrasonic energy having passed through the elastomer material; and an electronic control system configured to determine the transit time of the ultrasonic energy passing through the elastomer material, and to calculate one or more mechanical properties of the elastomer material based at least in part on the determined transit time.

According to some embodiments, the elastomer material is a component of a device used in a subsea or surface location in the oil and gas industry. Examples of the calculated mechanical properties of the elastomer material include: longitudinal modulus, bulk modulus, Poisson's ratio, and Young's modulus. The mechanical properties of the elastomer material can also be calculated based at determined longitudinal velocity of sound through the elastomer material. According to some embodiments, the mechanical properties can be used for quality control of a manufactured elastomer component made from the material.

According to some embodiments, the elastomer component can be used in a device such as a blow out preventer or a valve. The ultrasonic transducer(s) can be configured to be deployed within or near the device such that the mechanical properties can be determined for the elastomer material in situ. According to some embodiments, the ultrasonic transducer(s) can be formed within the device and/or conveyed through a wellbore as part of a toolstring. The transducer(s) can be used in pulse-echo mode and/or transmitter/receiver mode.

According to some embodiments, a method for characterizing elastomer material is described. The method includes: transmitting ultrasonic energy into an elastomer material being manufactured into a component of a device; receiving the ultrasonic energy having passed through the elastomer material; determining from the received ultrasonic energy a transit time of the ultrasonic energy passing through the elastomer material; calculating one or more mechanical properties of the elastomer material based at least in part on the determined transit time; and assessing quality of the manufactured component based on at least one of the calculated mechanical properties. According to some embodiments, the method can include assessing of quality of curing of the elastomer material.

According to some embodiments, a method is also described for characterizing elastomer material in situ. The method includes: transmitting ultrasonic energy into an elastomer material that forms a component of a device; receiving the ultrasonic energy having passed through the elastomer material; determining from the received ultrasonic energy a transit time of the ultrasonic energy passing through the elastomer material; calculating one or more mechanical properties of the elastomer material based at least in part on the determined transit time; and assessing degradation of the component in situ based at least in part on the calculated mechanical properties. According to some embodiments, the assessing of the degradation of the component includes assessing the component for fatigue due to temperature and/or pressure cycling.

BRIEF DESCRIPTION OF THE DRAWINGS

The subject disclosure is further described in the following detailed description, and the accompanying drawings and schematics of non-limiting embodiments of the subject disclosure. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

The particulars shown herein are for purposes of illustrative discussion of the embodiments of the present disclosure only. In this regard, no attempt is made to show structural details of the present disclosure in more detail than is necessary for the fundamental understanding of the present disclosure, the description taken with the drawings making apparent to those skilled in the art how the several forms of the present disclosure may be embodied in practice.

According to some embodiments, an ultrasonic system is configured to measure the velocity of sound in an elastomer. From the velocity measurement the quality of the elastomer can be determined during production and in situ. Examples of elastomers in the oil can gas industry includes packers, donuts, rubber seals and other molded flexible parts for BOPs, valves and other devices. According to some embodiments, the velocity of sound can be used to determine the mechanical properties of an elastomer, such as bulk modulus or Poisson's ratio. During manufacture and production of the elastomeric component the described method can be used as a quality assurance methodology to check the properties of the elastomer non-destructively. According to some embodiments, an ultrasonic sensor is placed near to (internally or externally to the BOP, valve or other device) the elastomer part, to measure the velocity of sound in situ. A single transducer can be configured to function in pulse echo mode for measuring the velocity of sound in the elastomer. From these measurements, fatigue of the elastomeric material, such as due temperature and pressure, can be monitored in situ. According to some embodiments, the properties of an elastomer which has failed from in the field can also be measured post mortem using ultrasonic transducer(s).

Figure 1:
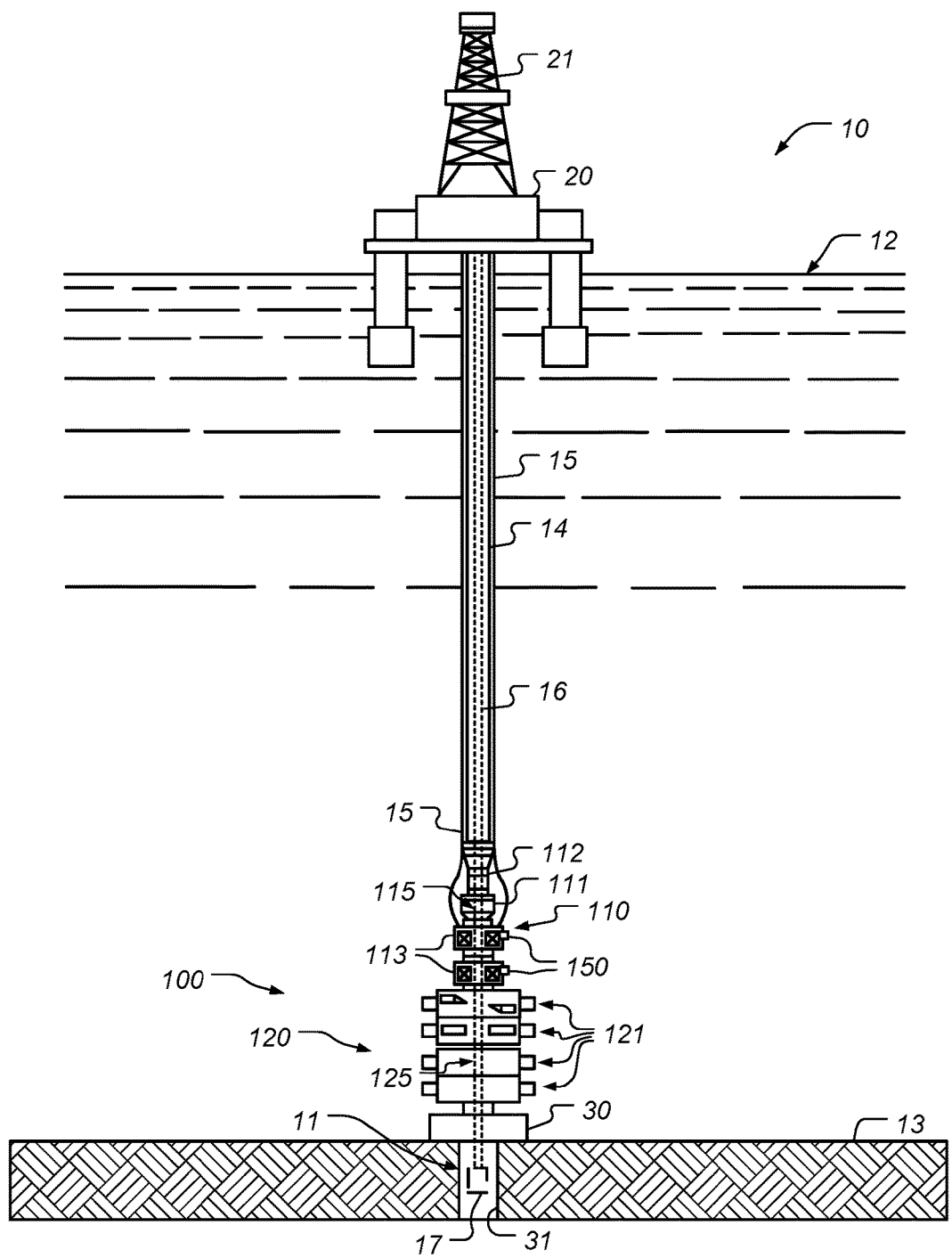
FIG. 1 is a diagram illustrating a drilling and/or producing wellsite where an elastomer characterization system could be deployed, according to some embodiments.

FIG. 1 is a diagram illustrating a drilling and/or producing wellsite where an elastomer characterization system could be deployed, according to some embodiments. In this example, an offshore system is being used to drill and/or produce from wellbore 11. The system includes an offshore vessel or platform 20 at the sea surface 12 and a subsea blowout preventer (BOP) stack assembly 100 mounted to a wellhead 30 at the sea floor 13. The platform 20 is equipped with a derrick 21 that supports a hoist (not shown). A tubular drilling riser 14 extends from the platform 20 to the BOP stack assembly 100. The riser 14 returns drilling fluid or mud to the platform 20 during drilling operations. One or more hydraulic conduit(s) 15 extend along the outside of the riser 14 from the platform 20 to the BOP stack assembly 100. The conduit(s) 15 supply pressurized hydraulic fluid to the assembly 100. Casing 31 extends from the wellhead 30 into the subterranean wellbore 11.

Downhole operations are carried out by a tubular string 16 (e.g., drillstring, production tubing string, coiled tubing, etc.) that is supported by the derrick 21 and extends from the platform 20 through the riser 14, through the BOP stack assembly 100, and into the wellbore 11. In this example, a downhole tool 17 is shown connected to the lower end of the tubular string 16. In general, the downhole tool 17 may comprise any suitable downhole tool(s) for drilling, completing, evaluating, and/or producing the wellbore 11 including, without limitation, drill bits, packers, cementing tools, casing or tubing running tools, testing equipment and/or perforating guns. During downhole operations, the string 16, and hence the tool 17 coupled thereto, may move axially, radially, and/or rotationally relative to the riser 14 and the BOP stack assembly 100.

The BOP stack assembly 100 is mounted to the wellhead 30 and is designed and configured to control and seal the wellbore 11, thereby containing the hydrocarbon fluids (liquids and gases) therein. In this example, the BOP stack assembly 100 comprises a lower marine riser package (LMRP) 110 and a BOP or BOP stack 120. The LMRP 110 includes a riser flex joint 111, a riser adapter 112, annular BOPs 113, and a pair of redundant control units or pods. A flow bore 115 extends through the LMRP 110 from the riser 14 at the upper end of the LMRP 110 to the connection at the lower end of the LMRP 110. The riser adapter 112 extends upward from the flex joint 111 and is coupled to the lower end of the riser 14. The flex joint 111 allows the riser adapter 112 and the riser 14 connected thereto to deflect angularly relative to the LMRP 110, while wellbore fluids flow from the wellbore 11 through the BOP stack assembly 100 into the riser 14. The annular BOPs 113 each include annular elastomeric sealing elements that are mechanically squeezed radially inward to seal on a tubular extending through the LMRP 110 (e.g., the string 16, casing, drillpipe, drill collar, etc.) or seal off the flow bore 115. Thus, the annular BOPs 113 have the ability to seal on a variety of pipe sizes and/or profiles, as well as perform a "Complete Shut-off" (CSO) to seal the flow bore 115 when no tubular is extending therethrough. According to some embodiments, each of the BOPs 113 includes an ultrasonic transducer 150 that are configured to make sonic measurements on the elastomeric sealing elements so that characterizations of their properties can be calculated.

In this embodiment, the BOP stack 120 comprises annular BOPs 113 as previously described, choke/kill valves, and choke/kill lines. A main bore 125 extends through the BOP stack 120. In addition, the BOP stack 120 includes a plurality of axially stacked ram BOPs 121. Each ram BOP 121 includes a pair of opposed rams and a pair of actuators that actuate and drive the matching rams. In this embodiment, the BOP stack 120 includes four ram BOPs 121—an upper ram BOP 121 including opposed blind shear rams or blades for severing the tubular string 16 and sealing off the wellbore 11 from the riser 14; and the three lower ram BOPs 120 including the opposed pipe rams for engaging the string 16 and sealing the annulus around the tubular string 16. In other embodiments, the BOP stack (e.g., the stack 120) may include a different number of rams, different types of rams, one or more annular BOPs, or combinations thereof.

Although FIG. 1 shows a wellsite setting where elastomer material is monitored in situ for fatigue due to temperature and pressure cycling, according to some embodiments, the ultrasonic measurements can also be used in the production of elastomer seals, donuts, packers, and etc. The measurements can be used to provide quality control information about the material properties of the manufactured rubber. It is important to know that materials being cured meet mechanical specifications during production.

Figure 2:
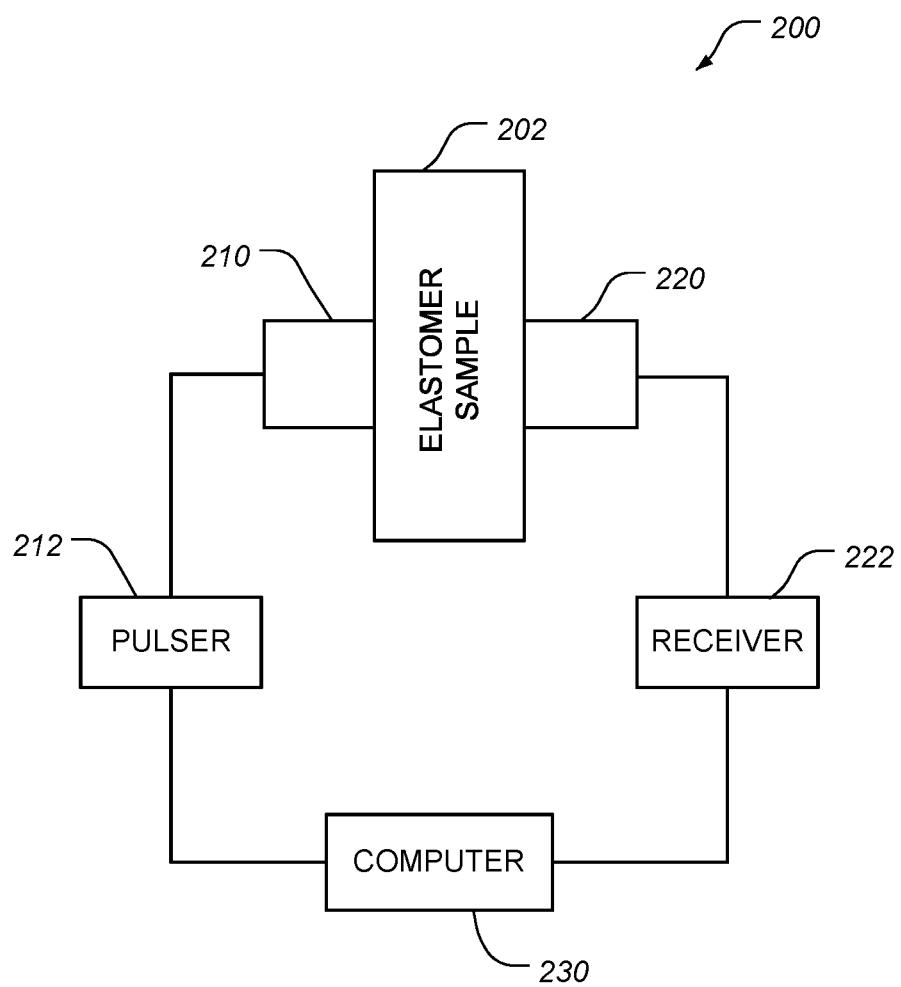
FIG. 2 shows an ultrasonic elastomer characterization system, according to some embodiments.

FIG. 2 shows an ultrasonic elastomer characterization system, according to some embodiments. The ultrasonic elastomer characterization system 200 includes piezoelectric transmitting and receiving transducers 210 and 220, pulser and receiver electronics 212 and 222 and computer 230. The system transmits and receives soundwaves through the elastomer sample 202. If the thickness of the elastomer 202 is known, the velocity of sound of the elastomer 202 can be calculated via the transit time measurement. The system 200 can be used to calculate mechanical properties such as longitudinal modulus, bulk modulus, and/or Poisson's ratio. The velocity of sound measurement is related to bulk modulus, shear modulus, and density of the elastomer. The velocity of sound is also an indicator of elastomer curing.

Figure 3:
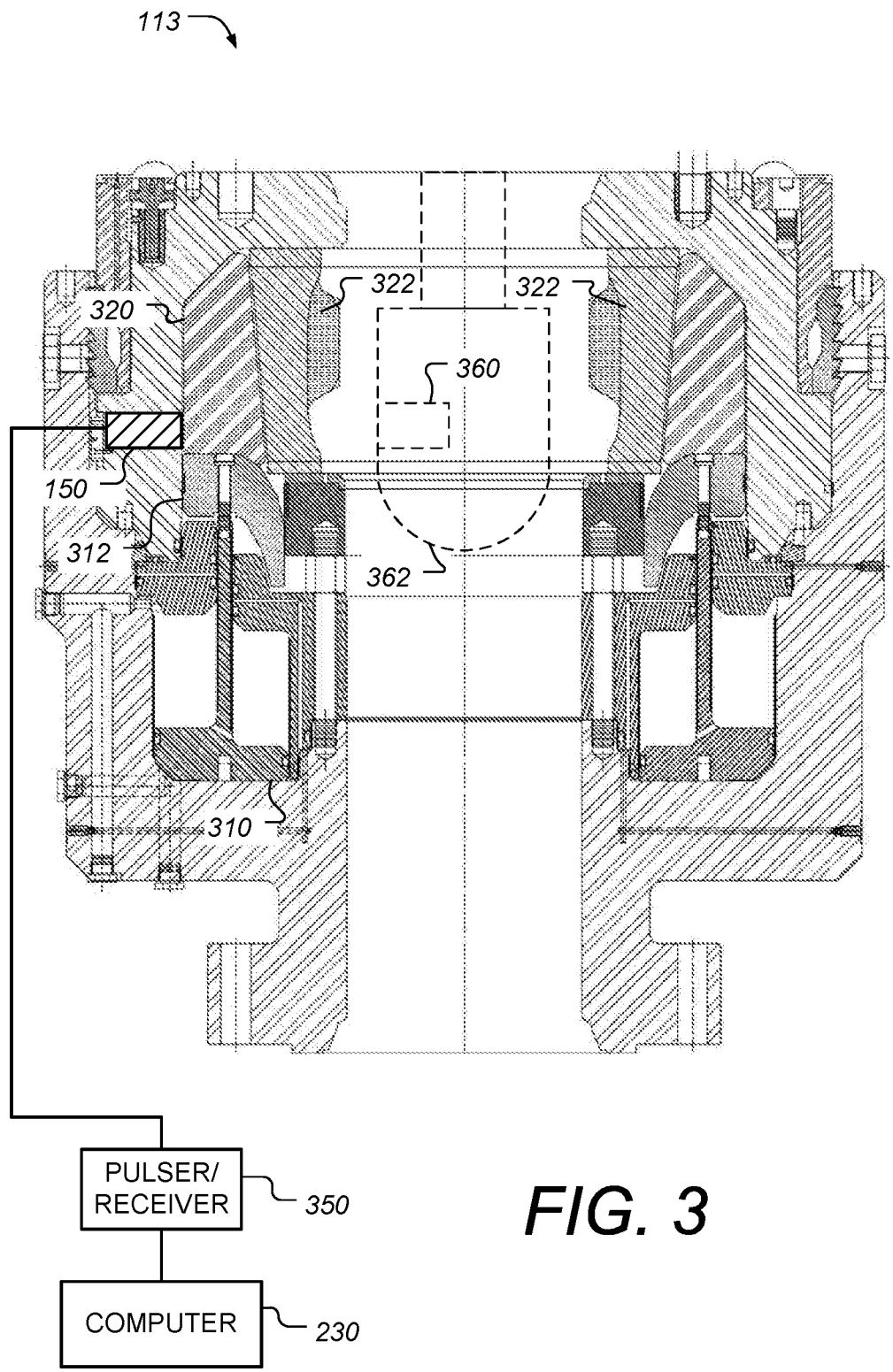
FIG. 3 is a diagram illustrating an annular BOP fitted with an ultrasonic transducer and electronic system configured to monitor elastomer components in situ, according to some embodiments.

FIG. 3 is a diagram illustrating an annular BOP fitted with an ultrasonic transducer and electronic system configured to monitor elastomer components in situ, according to some embodiments. Annular BOP 113 is shown in cross section. In this example, the BOP 113 includes two elastomer components: donut 320 and packer 322. In order to close and seal the BOP 113, hydraulic fluid enters below piston 310 and pushes it upwards. The piston lifts pusher plate 312, which in turn pushes on donut 320. The pressure on donut 320 forces the packer 322 radially inwards to form a seal with any tube within the BOP bore (or sealing off the bore if there is no tube or pipe present). To re-open the BOP, the hyrdaulic fluid enters above the piston thereby forcing it back downwards. In some embodiments, separate pistons can be used for opening and closing the BOP. The ultrasonic transducer 150, pulser/receiver 350 and computer 230 in thisse are configured to operate in pulse echo mode. The received signals indicate the time between the initial pulse and echos from the walls of the donut 320 and packer 322. From the time of flight the velocity of sound can be determined, and the mechanical properties such as longitudinal modulus, bulk modulus, and/or Poisson's ratio of donut 320 and/or packer 322 can be calculated. According to some embodiments, this real-time monitoring system can be used to make measurements before and after each usage of the BOP in order to evaluate the elastic properties of the elastomers due to fatigue. Although the transducer 150 is positioned as shown in FIG. 3, other mounting locations with the BOP 113 are possible. Additionally, according to some embodiments, a plurality of ultrasonic transducers are included in BOP 113 at various locations. According to some embodiments, an ultrasonic transducer 360 can be conveyed on a tool 362 positioned within the BOP, such as shown in dashed outline in FIG. 3. The tool can be conveyed on a wireline, such as the Schlumberger's USI Ultrasonic Imager Tool, or it could be conveyed in other ways such as part of a drillstring or on coiled tubing. According to some embodiments, the transducer 360 could be used instead of a BOP mounted transducer, and according to other embodiments, it could be used in combination with one or more BOP mounted transducers to make the acoustic measurements of the elastomer components as described herein.

Figure 4A:
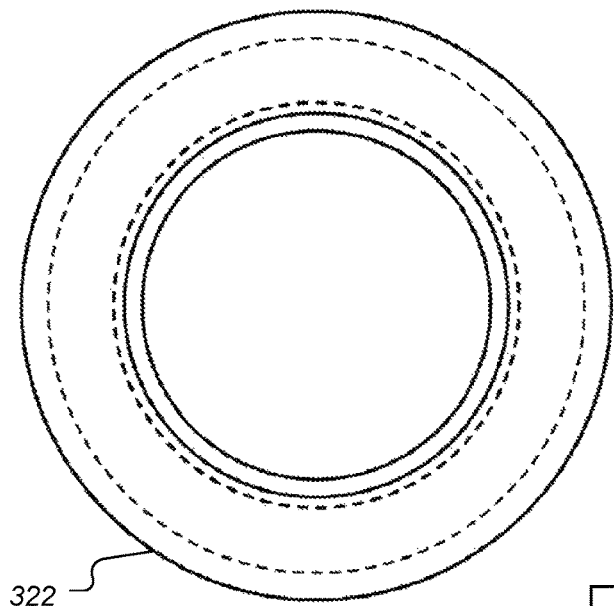
FIGS. 4A and 4B are diagrams showing a system for ultrasonically testing a packer during production for quality assurance purposes, according to some embodiments.
Figure 4B:
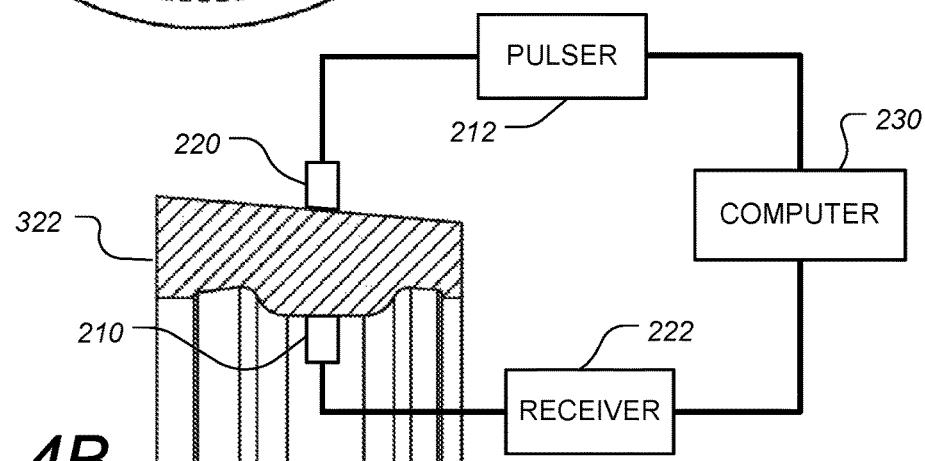
Figure 4B:
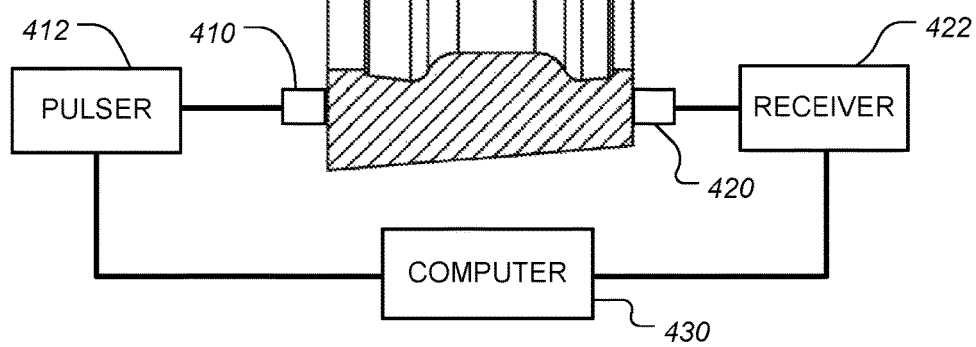

FIGS. 4A and 4B are diagrams showing a system for ultrasonically testing a packer during production for quality assurance purposes, according to some embodiments. FIG. 4A is a top view of a packer 322, which according to some embodiments, is a packer for use in an annular BOP, such as shown in FIGS. 1 and 3. FIG. 4B is a cross section of the packer 322 showing ultrasonic transducers arranged to make acoustic measurements for quality assurance purposes during manufacture of the packer. In particular, a pair of sending and receiving transceivers 210 and 220 are arranged on the inner and outer surfaces of the packer, respectively as shown. The pulser 212, receiver 222, and computer 230 can be used to make the measurements as described supra with respect to FIG. 2. Additionally, another pair of sending and receiving transceivers 410 and 420 are arranged on the upper and lower surfaces of the packer 322, as shown, along with pulser 412, receiver 422, and computer 430 for make further acoustic measurements of the elastomer material.

Figure 5A:
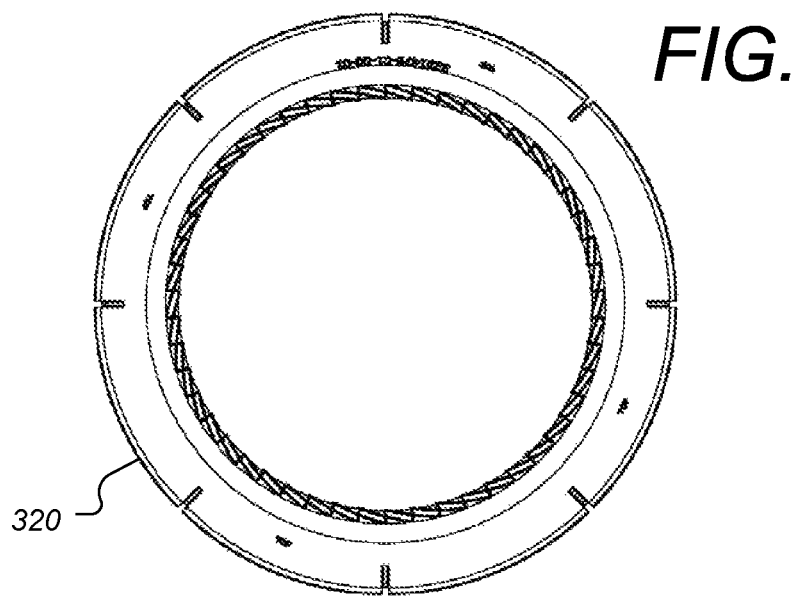
FIGS. 5A and 5B are diagrams showing a system for ultrasonically testing a donut during production for quality assurance purposes, according to some embodiments.
Figure 5B:
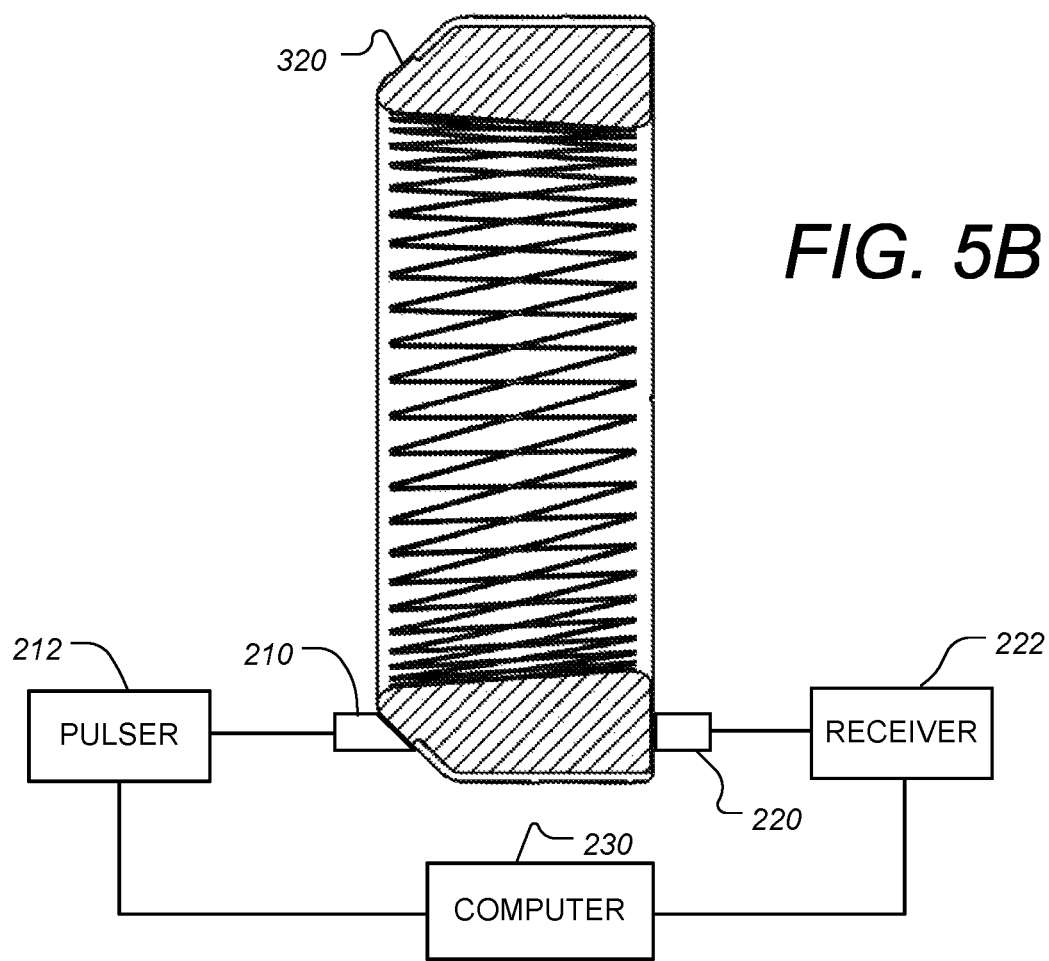

FIGS. 5A and 5B are diagrams showing a system for ultrasonically testing a donut during production for quality assurance purposes, according to some embodiments. FIG. 5A is a top view of a donut 320, which according to some embodiments is a donut for use in an annular BOP, such as shown in FIGS. 1 and 3. FIG. 5B is a cross section of the donut 320 showing ultrasonic transducers arranged to make acoustic measurements for quality assurance purposes during manufacture of the packer. In particular, a pair of sending and receiving transceivers 210 and 220 are arranged on the upper and lower surfaces of the donut, respectively as shown. The pulser 212, receiver 222, and computer 230 can be used to make the measurements as described supra with respect to FIG. 2. Although specific locations of the transducers are shown in FIGS. 4B and 5B, according to some embodiments, other locations and other numbers of transducers can be used to make the acoustic measurements of the elastomer material as described herein.

According to some embodiments, the ultrasonic measurement techniques described herein can be used for port mortem analysis of elastomer components after being retired from use and/or removed following a failure. Such analysis would be useful in planning for replacement components, as well as reducing risk of future failures.

Figure 6A:
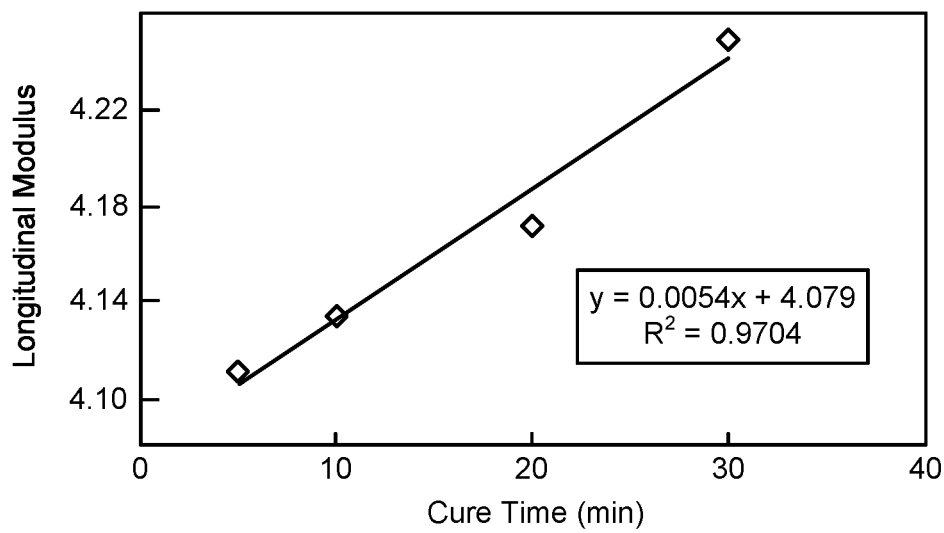
FIGS. 6A-6D are graphs plotting cure time versus longitudinal modulus for four elastomer compounds.
Figure 6B:
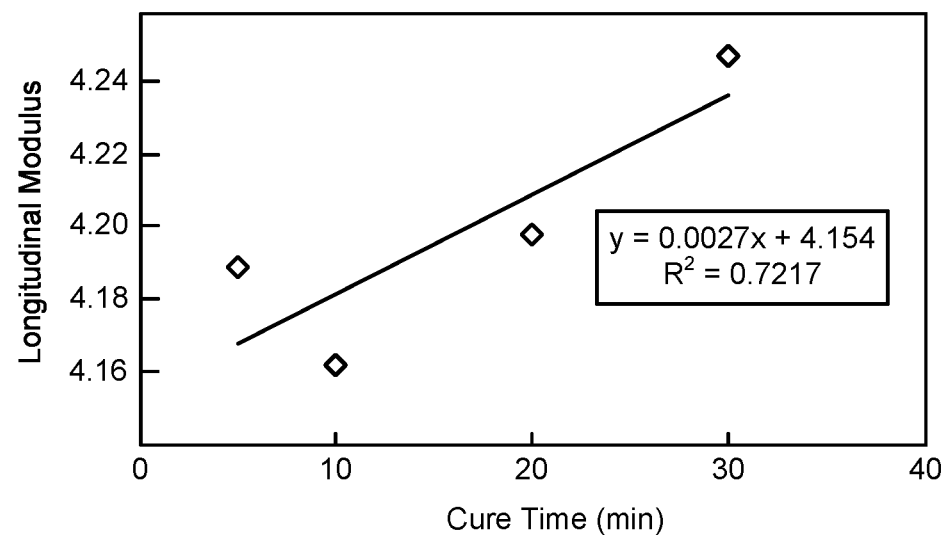
Figure 6C:
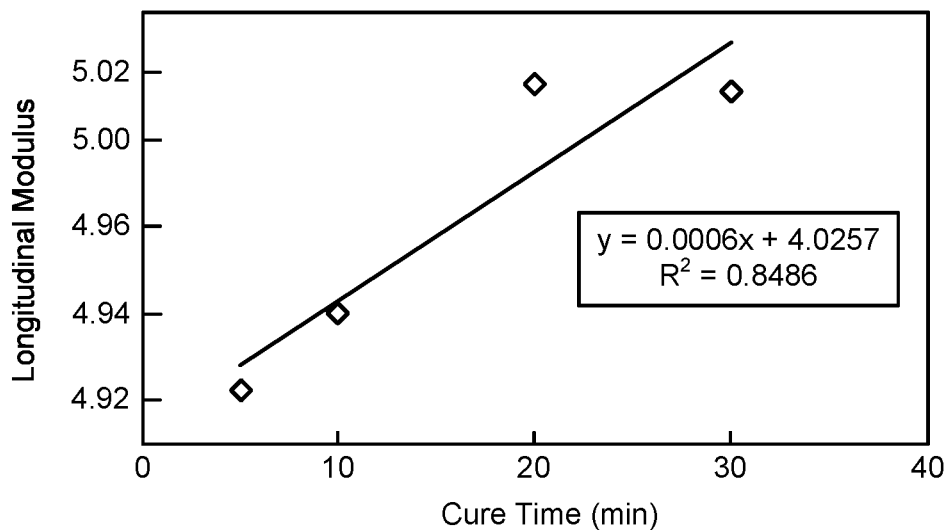
Figure 6D:
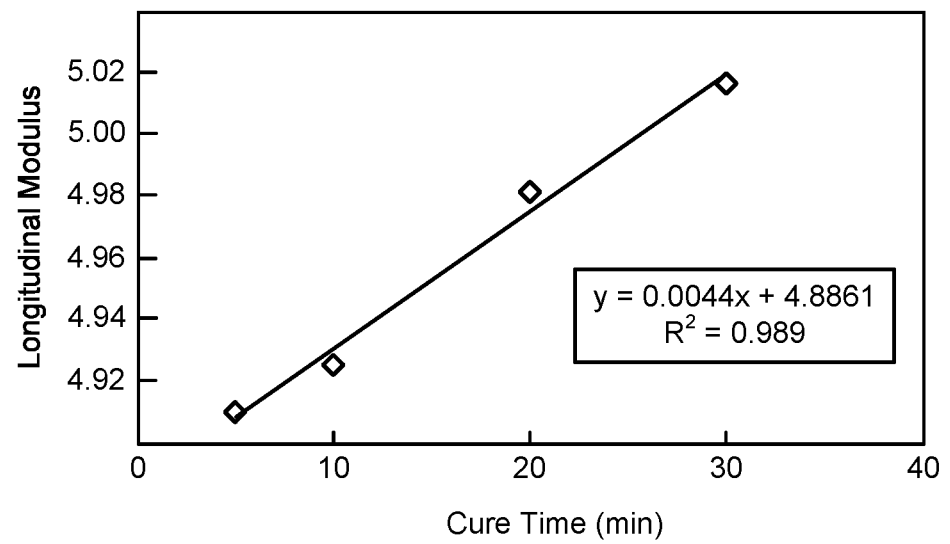

FIGS. 6A-6D are graphs plotting cure time versus longitudinal modulus for four elastomer compounds. As can be seen, there is a high correlation between the cure time and longitudinal modulus for the compounds plotted. For each of the data points shown on the plots in FIGS. 6A-6D, ultrasonic time of flight measurements and density measurements were used to determine the longitudinal modulus. FIGS. 6A, 6B and 6D are plots for three different formulations of HNBR polymer, while FIG. 6C is a plot of an NBR polymer. The following measurements were made for one formulation of HNBR virgin elastomer (i.e. before being used in service) the bulk modulus=3.468 GPa, Young's modulus=0 and Poisson's ratio=0.5. The shear modulus is assumed to be very small compared to the Bulk modulus. The virgin elastomer weight was 7.90 grams and volume=7 ml. The density (Mass/Volume) was therefore=1.128 g/ml~1.13 g/cc=1130 Kg/m$^3$. A 3.5 MHz ultrasonic transducer was used. The elastomer thickness was 0.0075438 meter. The time of flight (i.e. transit time−non-fluid time delay) was 4.64×10$^{-6}$ seconds−335×10$^{-9}$ seconds=4.305×10$^{-6}$ seconds. The longitudinal velocity (Thickness/Time of flight) was therefore 1752 meters per second. The longitudinal modulus (L) is equal to the density×(Longitudinal Velocity)$^2$=1130 Kg/m$^3$×(1752 m/s)$^2$=3.468×10$^6$ Kg/(ms$^2$)=3.468 GPa. Other mechanical properties for the virgin elastomer were: Shear Modulus (G)=Density×(Shear Velocity)$^2$~0; Bulk Modulus (K)=L−(4/3)G=L=3.468 GPa; Poisson's Ratio ($\sigma$)=(L−2G)/2(L−G)=0.5; Young's Modulus (E)=2G (1+$\sigma$) ~0; and Hardness (H)=(1−2$\sigma$) E/(6(1+$\sigma$))~0.

According to some embodiments, other elastomer components can be monitored using the ultrasonic measurements described herein. For example, in the oil and gas industry common uses of elastomer include rubber seals and molded flexible parts deployed in components on the surface, subsea or within a wellbore, such as in valves. Examples of such valves include: butterfly valves; valve stems; grove ball valves; WKM gate valves; threaded ball valves; chokes; and surface gate valves.

According to some embodiments, elastomer material is monitored during production, in situ during use, and/or post mortem, in industries and applications other other than the oil and gas industry. Examples include monitoring pneumatic and solid rubber tires used in vehicles such as cars, motorcycles, buses, trucks, heavy equipment and aircraft. The techniques described herein can be used for quality control purposes during the manufacture of such tires, during use to monitor aging of such tires, as well as post mortem following use and/or failure of such tires.

According to some embodiments, the elastomer material characterized using the ultrasonic measurements as described herein can in general be any type of polymer with viscoelasticity, and includes natural and synthetic rubber material. Examples of synthetic elastomer material include: synthetic polyisoprene; polybutadiene; chloroprene rubber; polychloroprene, neoprene; baypren; butyl rubber; halogenated butyl rubbers; styrene-butadiene Rubber; nitrile rubber (also called Buna N rubber); hydrogenated nitrile rubbers (HNBR); EPM (ethylene propylene rubber; EPDM rubber (ethylene propylene diene rubber); epichlorohydrin rubber (ECO); polyacrylic rubber (ACM, ABR); silicone rubber (SI, Q, VMQ); fluorosilicone rubber (FVMQ); fluoroelastomers (FKM, and FEPM); perfluoroelastomers (FFKM); polyether block amides (PEBA); chlorosulfonated polyethylene (CSM); and ethylene-vinyl acetate.

While the subject disclosure is described through the above embodiments, it will be understood by those of ordinary skill in the art, that modification to and variation of the illustrated embodiments may be made without departing from the concepts herein disclosed.

What is claimed is:

1. A system for characterizing an elastomer material that forms a component of a device configured for use at a wellsite, the system comprising:
   one or more ultrasonic transducers coupled to a housing of the device, wherein the one or more ultrasonic transducers are configured to transmit ultrasonic energy into the elastomer material and to receive the ultrasonic energy having passed through the elastomer material; and
   an electronic control system configured to determine a transit time of the ultrasonic energy passing through the elastomer material and to calculate one or more mechanical properties of the elastomer material based at least in part on the determined transit time.

2. A system according to claim 1 wherein the one or more mechanical properties of the elastomer material are selected from a group consisting of:
   longitudinal modulus, bulk modulus, Poisson's ratio, and Young's modulus.

3. A system according to claim 1 wherein the electronic control system is further configured to calculate longitudinal velocity of sound through the elastomer material and the one or more mechanical properties of the elastomer material based at least in part on the calculated longitudinal velocity.

4. A system according to claim 1 wherein the device is selected from a group consisting of: a blow out preventer and a valve.

5. A system according to claim 1 wherein the one or more ultrasonic transducers are positioned within the housing of the device to facilitate determination of the one or more mechanical properties of the elastomer material by the electronic control system in situ.

6. A system according to claim 5 wherein the wellsite comprises a subsea wellsite, and the device is deployed at the subsea wellsite.

7. A system according to claim 1 wherein the one or more ultrasonic transducers is coupled to a toolstring to enable the one or more ultrasonic transducers to be conveyed through a wellbore with the toolstring.

8. A system according to claim 1 wherein the one or more ultrasonic transducers is a single transducer that is configured to operate in pulse echo mode.

9. A method for characterizing elastomer material comprising:
   transmitting, from one or more ultrasonic transducers, ultrasonic energy into an elastomer material being manufactured into a component of a device;
   receiving, at the one or more ultrasonic transducers, the ultrasonic energy having passed through the elastomer material;
   determining using an electronic control system, a transit time of the ultrasonic energy passing through the elastomer material based at least in part on the received ultrasonic energy;
   calculating, using the electronic control system, one or more mechanical properties of the elastomer material based at least in part on the determined transit time; and
   assessing, using the electronic control system, a quality of the manufactured component based at least in part on the one or more calculated mechanical properties.

10. A method according to claim 9 further comprising calculating longitudinal velocity of sound through the elastomer material, wherein the one or more mechanical properties of the elastomer material are based at least in part on the calculated longitudinal velocity, and are selected from a group consisting of longitudinal modulus, bulk modulus, Poisson's ratio, and Young's modulus.

11. A method according to claim 9 wherein the component comprises an annular packer, wherein the device comprises an annular blow out preventer configured for use at a wellsite in the oil and gas industry, wherein the one or more ultrasonic transducers comprise a first ultrasonic transducer and a second ultrasonic transducer, wherein one of the first or second ultrasonic transducers are positioned at a radially-outer surface of the annular packer and the other one of the first or second ultrasonic transducers are positioned at a radially-inner surface of the annular packer, wherein transmitting the ultrasonic energy from the one or more transducers comprises transmitting the ultrasonic energy from the first ultrasonic transducer, and wherein receiving the ultrasonic energy comprises receiving the ultrasonic energy at the second ultrasonic transducer.

12. A method according to claim 9 wherein calculating the one or more mechanical properties comprises calculating a longitudinal modulus based on the determined transit time and a density of the elastomer material, and wherein assessing the quality of the manufactured component comprises assessing the quality of curing of the elastomer material based on the longitudinal modulus.

13. A method for characterizing elastomer material in situ comprising:
   transmitting, from one or more ultrasonic transducers, ultrasonic energy into an elastomer material that forms a component of a device;
   receiving at the one or more ultrasonic transducers, the ultrasonic energy having passed through the elastomer material;
   determining, using an electronic control system, a transit time of the ultrasonic energy passing through the elastomer material based at least in part on the received ultrasonic energy;
   calculating, using the electronic control system, one or more mechanical properties of the elastomer material based at least in part on the determined transit time; and
   assessing, using the electronic control system, degradation of the component in situ based at least in part on the one or more calculated mechanical properties.

14. A method according to claim 13 further comprising calculating longitudinal velocity of sound through the elastomer material, wherein the one or more mechanical properties of the elastomer material are based at least in part on the calculated longitudinal velocity, and are selected from a group consisting of longitudinal modulus, bulk modulus, Poisson's ratio, and Young's modulus.

15. A method according to claim 13 wherein the device comprises a blowout preventer or a valve deployed at a wellsite used in the oil and gas industry.

16. A method according to claim 13 wherein the the device is deployed at a subsea wellsite.

17. A method according to claim 13 wherein assessing the degradation of the component comprises assessing the component for fatigue due to temperature and/or pressure cycling.

18. The system of claim 1 wherein the component comprises an annular component, the device comprises an annular blow out preventer, the one or more ultrasonic transducers comprises a first ultrasonic transducer that is positioned proximate to a radially-outer surface of the annular component.

19. The system of claim 18, wherein the first ultrasonic transducer is configured to operate in pulse echo mode to transmit the ultrasonic energy into the elastomer material and to receive the ultrasonic energy having passed through the elastomer material to enable the electronic control system to determine the transit time of the ultrasonic energy.

20. The method of claim 15, comprising carrying out the steps of the method following use of the blow out preventer or the valve during drilling or production operations.

\* \* \* \* \*